(12) United States Patent
Young et al.

(10) Patent No.: US 7,735,369 B2
(45) Date of Patent: Jun. 15, 2010

(54) IMMERSION ULTRASONIC TEST PART HOLDER, SYSTEM AND METHOD FOR NONDESTRUCTIVE EVALUATION

(75) Inventors: Fred D. Young, Bellevue, WA (US); Martin L. Freet, Federal Way, WA (US); Kevin R. Bray, Seattle, WA (US)

(73) Assignee: The Boeing Company, Chicago, IL (US)

( * ) Notice: Subject to any disclaimer, the term of this patent is extended or adjusted under 35 U.S.C. 154(b) by 434 days.

(21) Appl. No.: 11/843,471

(22) Filed: Aug. 22, 2007

(65) Prior Publication Data

US 2009/0049920 A1 Feb. 26, 2009

(51) Int. Cl.
*G01N 29/06* (2006.01)
*G01N 29/26* (2006.01)
(52) U.S. Cl. .......................................... 73/622; 73/644
(58) Field of Classification Search .................. 73/620, 73/622, 644
See application file for complete search history.

(56) References Cited

U.S. PATENT DOCUMENTS

| 4,055,988 | A | * | 11/1977 | Dutton, Jr. ................. | 73/620 |
| 5,629,865 | A | * | 5/1997 | Roth ............................ | 702/56 |
| 5,700,955 | A | * | 12/1997 | Roth ............................ | 73/597 |
| 6,065,343 | A | * | 5/2000 | Kiuchi et al. ............... | 73/622 |
| 6,301,512 | B1 | | 10/2001 | Motzer | |
| 6,658,939 | B2 | | 12/2003 | Georgeson et al. | |
| 6,993,971 | B2 | | 2/2006 | Bossi et al. | |
| 7,216,544 | B2 | | 5/2007 | Vacarro et al. | |
| 7,240,556 | B2 | | 7/2007 | Georgeson et al. | |
| 2005/0061077 | A1 | * | 3/2005 | Ziola et al. .................. | 73/622 |
| 2008/0041160 | A1 | * | 2/2008 | Wright ......................... | 73/622 |

FOREIGN PATENT DOCUMENTS

CA 2127039 A1 3/1996

OTHER PUBLICATIONS

Olympus NDT; Aqualene Elastomer Couplant; http://www.olympusndt.com/en/products/ndt-other/aqualene; 2007; 1 page.
Bourne, S., et al.; Novel Solid Contact Ultrasonic Couplants Based on Hydrophilic Polymers; http://www.ndt.net/article/wcndt00/papers/idn406/idn406.htm; AIPnD; 13 pages.
Yochev, B., et al.; Investigation of Ultrasonic Properties of Hydrophilic Polymers for Dry-Coupled Inspection; ECNDT 2006-We.1.6.5; 13 pages.
Key to Metals AG; Ultrasonic Testing of Safety Parts in Automobile Manufacturing; http://www.key-to-steel.com; 1999-2007; 3 pages.
Ginzel, E.A., et al.; Ultrasonic Properties of a New Low Attenuation Dry Couplant Elastomer; Apr. 1994; Ginzel Brothers & Associates Ltd.; 10 pages.

* cited by examiner

*Primary Examiner*—Hezron Williams
*Assistant Examiner*—Rose M Miller
(74) *Attorney, Agent, or Firm*—Armstrong Teasdale LLP

(57) ABSTRACT

A part holder for immersion ultrasonic testing having a solid buffer material with acoustic properties that match the immersion fluid is disclosed. Test systems and methods are also disclosed.

20 Claims, 6 Drawing Sheets

IMMERSION ULTRASONIC TEST PART HOLDER, SYSTEM AND METHOD FOR NONDESTRUCTIVE EVALUATION

BACKGROUND OF THE DISCLOSURE

This disclosure relates generally to test equipment for nondestructive evaluation systems, and more specifically to wet-coupled ultrasonic evaluation systems for the inspection of parts.

As new materials, such as composite materials, are used in more applications throughout the aircraft industry and other industries, the use of nondestructive test equipment, such as ultrasonic test equipment, to inspect fabricated parts prior to use has become widespread. Ultrasonic test equipment allows an operator to nondestructively inspect the interior of parts, such as fuselage or wing components, for areas of discontinuity such as structural inconsistencies, imperfections, delaminations, foreign objects introduced during fabrication, etc.

Ultrasonic test equipment utilizes a high frequency sound wave generated by an ultrasonic transducer, sometimes referred to as a probe, that is located near the surface of the part being tested. The ultrasonic transducer is oriented such that the high frequency sound wave travels through the part, usually in the height or thickness direction. When the sound wave encounters a discontinuity, such as a delamination, or a change in the stiffness of the material, part of the sound energy is reflected. The reflected sound energy travels back through the part and is received by the same ultrasonic transducer, which acts as both a transmitter and receiver in what is commonly referred to as a "pulse echo" ultrasonic test system. Alternatively, the high frequency sound wave generated by the ultrasonic transmitter passes through the entire thickness of the part and is received on the opposite side of the part by a separate receiver in what is commonly known as "through transmission" ultrasonic testing. Pulse echo ultrasonic testing is the most common technique in use because access to only one side of a part is required.

The waveform of the received RF signal from an ultrasonic test is recorded by the test equipment and/or displayed on a monitor or other display device. The data contained in the RF signal can be displayed in a number of different formats for review by technicians. Any distortion in received signals can be an impediment to effective use of the test system to identify potential unwanted discontinuities in the part being tested. Distortion and/or interference in the received signals is particularly problematic when it leads an operator or technician to falsely believe that a discontinuity is present.

The production of a large variety of relatively small, low volume parts produces an extra set of challenges for nondestructive inspection. Conventionally, custom designed part holders unique to each part that is to be inspected are utilized. Such customized part holders may typically support the ends of the part, leaving the center free from obstruction, such that only a very small portion of the part will be in actual contact with the fixture. Such customized part holders are undesirable, however, when many different parts are being ultrasonically scanned for inspection purposes. For example, in an aircraft assembly, as many as 80 different structural parts of varying shape and size are assembled to define a portion of an aircraft. Preferably, each of the 80 structural parts needs to be scanned and inspected to ensure the structural integrity thereof. Creating a specialized part holder for each of the 80 parts would be costly, time consuming, and generally impractical for the relatively low volume of parts involved to produce a limited number of aircraft.

It would be desirable to form a more universally usable part holder for ultrasonic testing that may be reliably used with a variety of parts without adversely affecting the test results.

BRIEF SUMMARY

Consistent with illustrative embodiments disclosed, a part holder for ultrasonic testing of a part to be inspected that is immersed in a fluid is disclosed. The part is to be inspected with an ultrasonic scanning probe, and the part holder comprises: at least a first surface for holding of the part in a predetermined orientation relative to the ultrasonic scanning probe; and a portion of the first and second support surfaces provided with a solid buffer material having acoustic properties approximately equal to the immersion fluid, the solid material separating a surface of the part from the first surface to reduce signal distortion caused by the first surface.

Optionally, the solid buffer material may comprise one of an elastomeric material and a hydrophilic polymer. The solid buffer material may comprise a first strip and a second strip spaced from one another on the first surface. The first surface may be substantially planar, and the part holder is rotatable about a longitudinal axis thereof to adjust the predetermined position. The part holder may further comprises at least a second surface for holding of the part in a predetermined orientation relative to the ultrasonic scanning probe, the second surface separated from the first surface and spaced from the first surface, and the second surface provided with the solid buffer material to separate a surface of the part from the second support surface. A third surface for holding of the part in a predetermined orientation relative to the ultrasonic scanning probe may also be provided, the third surface separated from the first and second surfaces and spaced from each of the first and second surfaces, and the third surface also provided with the solid buffer material to separate a surface of the part from the third support surface. The second surface may be positioned between the first and third surfaces, the first and third surfaces supporting an end portion of the part and the second surface supporting a portion of the part between the end portions. The part may be retained to the solid buffer material solely by frictional forces, and the solid buffer material may exhibit the acoustic properties of water.

In another embodiment, an ultrasonic test system for the inspection of a variety of differently shaped parts is disclosed. The test system comprises: an immersion tank constructed to be filled with an immersion fluid; a part holder in the immersion tank, the part holder comprising a plurality of surfaces for maintaining the part in a predetermined position within the tank, each of the surfaces being provided with a solid buffer material covering at least part of the respective part thereof, the solid buffer material defining raised support surfaces for the part and the solid buffer material having acoustic properties approximately equal to acoustic properties of the immersion fluid; and an ultrasonic probe movable along an outer surface of the part when the part is placed upon the raised support surfaces. Ultrasonic waves generated by the probe are passed first through the part and secondly through the solid buffer material to separate echoes from the part from echoes of the support surfaces.

Optionally, the solid material may comprise one of an elastomeric material and a hydrophilic polymer. Each of the surfaces of the part holder may be substantially flat. The surfaces of the part holder may be separated from one another along a length of the part. The solid material may be applied to the surfaces of the part holder in strips separated from one another. The surfaces of the part holder may support the part on a first end, a second end, and an intermediate portion between the first end and the second end. The part holder may be rotatable to selectively position the surfaces at different angles relative to the ultrasonic probe.

According to another embodiment, a method of inspecting parts with an ultrasonic test system is disclosed. The test system includes an ultrasonic probe, an immersion tank and an immersion fluid in the tank, and a part holder submerged in the immersion tank, The part holder has a plurality of separated surfaces thereon for accommodating a variety of parts to be inspected, and the part holder is rotatable to selectively position the surfaces of the part holder relative to the ultrasonic probe. The method comprises: positioning a part upon at least two surfaces of the part holder; rotating the part to a desired position relative to the ultrasonic probe; utilizing the ultrasonic probe to generate a high frequency sound wave near a surface of the part; collecting return echoes of the part with the ultrasonic probe; and separating the return echoes of the part from the return echoes of the at least two surfaces of the part holder.

Optionally, the separating of the return echoes comprises: providing the at least two surfaces with a solid material having acoustic properties approximately equal to the acoustic properties of the immersion fluid, with the solid material extending between the surfaces of the part holder and the part, thereby creating an acoustic delay between a return echo of the part and a return echo of the part holder. Providing the at least two surfaces with dielectric material may comprise applying strips of the solid material to the surfaces of the part holder.

BRIEF DESCRIPTION OF THE DRAWINGS

Non-limiting and non-exhaustive embodiments are described with reference to the following Figures, wherein like reference numerals refer to like parts throughout the various views unless otherwise specified.

DETAILED DESCRIPTION

Exemplary embodiments of versatile and easy to use ultrasonic test systems, new and inventive part holders therefor, and methods of inspecting parts are disclosed hereinbelow that facilitate ultrasonic inspection of a variety of parts with minimal signal distortion. Thus, customized part holders, and associated cost and manufacturing resources that they present, may be avoided. Reduced costs for tooling required for the testing, and increased production rates are therefore possible. Additionally, an improved test signal quality allows for increased sensitivity of the ultrasonic scanning system, both increasing the ability to find structural inconsistencies and reducing waste due to false positive indications of discontinuities.

These and other advantages may be obtained with the provision of an immersion tank that allows wet coupling of an ultrasonic transducer or probe to a wide variety of different part geometries. A part holder is provided that includes a solid material having acoustic impedance properties similar to that of the immersion coupling fluid being used, such as a hydrophilic elastomer when the coupling fluid is water. The solid material separates a part that is being inspected from the part holder, creating a gap or clearance between the part holder and the part being tested. The material is acoustically invisible to the ultrasonic scan, and substantially avoids, or at least minimizes, signal interference and distortion attributable to the part holder may otherwise be present in the test results. The part holder is described in detail hereinbelow after some introduction to particular problems in the art relating to signal interference and distortion issues.

Figure 1:
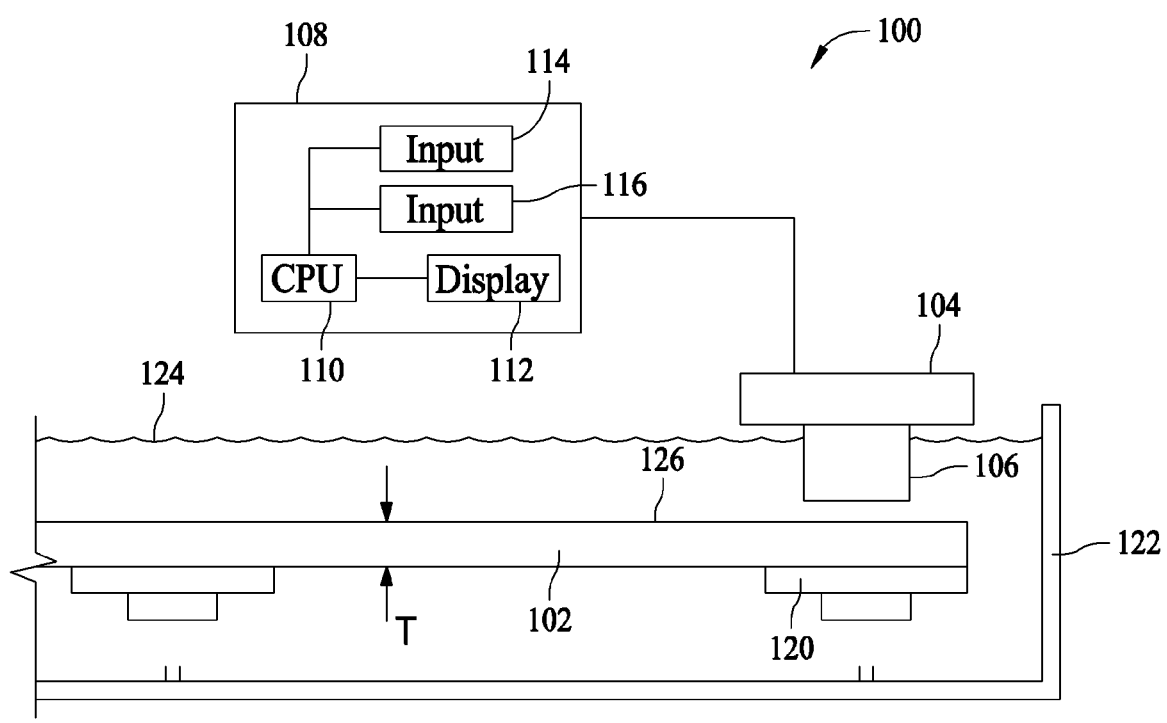
FIG. 1 is schematically represents an exemplary nondestructive test system.

FIG. 1 schematically represents an exemplary nondestructive test system 100 for acquiring, analyzing and displaying ultrasonic test data for inspection of a part 102. The system 100 includes an ultrasonic test apparatus 104 that includes electrical and mechanical components and an ultrasonic transducer, sometimes referred to as a probe 106. The ultrasonic test apparatus 104 is connected to a computer system 108 that includes a central processing unit (CPU) 110, a display 112, and input devices 114, and 116, which in an exemplary embodiment may be a mouse and a keyboard, respectively.

The ultrasonic test apparatus 104 may take the form of any ultrasonic test equipment known to those skilled in the ultrasonic testing art. The apparatus 104 is capable of scanning different materials and parts for discontinuities including inconsistencies or areas of delamination, etc. As is well known to those skilled in the ultrasonic test art, different types of industrial ultrasound tests are used to conduct through transmission ultrasound (TTU) and pulse echo (PE) ultrasound tests. In a TTU test, sound waves produced by an ultrasonic transmitter located on one side of the part and received by a receiver located on the opposite side of the part pass completely through the part. On the other hand, a PE ultrasound test apparatus uses a single transducer or probe 106 located on one side of the part 102, with the probe 106 functioning as both a transmitter and a receiver. Pulse echo testing is preferred because access to only one side of the test part 102 is required. In any event, ultrasonic test apparatus 104, in addition to one or more ultrasonic transducer or probes 106, includes known interface electronics that perform appropriate signal processing and, usually, an electromechanical apparatus for moving the probe 106 across the surface of the part 102 to be tested. Frequently, the electromechanical scanning apparatus 104 includes position sensors (not shown) that monitor the position of the moving transducer relative to the part 102. In another embodiment, however, the apparatus 104 may be manually moved over the part 102 for inspection purposes.

As also schematically represented in FIG. 1, the part 102 is typically supported by a fixture or part holder 120. The part holder 120 and the part 102 may be located within a fluid filled tank 122 and submerged in, for example, a coupling fluid 124 such as water to a predetermined depth. The probe 106 and the part 102 are submerged to establish a continual water path between the probe 106 the part 102, along which the ultrasound propagates. Thus, the fluid 124 is the coupling media in one example, and maintains a constant level of coupling and consistent sensitivity of the system 100. While water is a preferred fluid 124 in one example, other coupling fluids may likewise be utilized in other embodiments if desired.

It is noted that when the part 102 is elongated, the part holder 120 typically supports the part 102 only partly along its axial length. That is, a portion of the part 102 rests upon the part holder 120 with surface-to-surface engagement, and another portion of the part 102 is cantilevered relative to the part holder 120 and overhangs the part holder 120. The part 102 may extend for a number of feet, with the part holder 120 supporting the part 102 at various, regularly spaced intervals along the length of the part 102. In one example the tank 122 may be about ten feet long and about two feet wide, with the part holder 120 and the part 102 extending up to the length of the tank 122.

In an exemplary embodiment, the fixture or part holder 120 may be fabricated from stainless steel that is generally corrosion resistant for use in the immersion tank 122, or alternatively, from another known material suitable for use with an ultrasonic testing system. The test part 102 may be fabricated from a different material than the part holder 120. For example, that part 102 may be fabricated a carbon fiber-reinforced resin composite material that advantageously provides high structural strength with a much lighter overall weight of the part 102 than comparable parts fabricated from metallic materials such as structural steel. The part 102 may be fabricated using known methods and techniques, and subsequently brought to the test system 100 for inspection, evaluation, and analysis.

The part 102 may be a structural component of an aircraft or another vehicle, including automobiles, trucks, buses, recreational vehicles, and marine applications as several examples. While some examples of parts 102 are particularly noted, it is appreciated that parts 102 having other applications apart from vehicles, and also parts 102 fabricated from various other materials familiar to those in the art, may likewise be evaluated using the techniques described hereinbelow.

In a pulse echo ultrasound apparatus 104, a high frequency sound wave generated by the ultrasonic probe 106 passes through the fluid 124 covering the part 102, and enters the test part 102 at the location(s) where test data is desired. As the high frequency sound wave passes through the thickness (indicated by the dimension T shown in FIG. 1) of the test part 102, the sound wave comes into contact with any areas of discontinuity located in the path of the wave. Such discontinuities could include a void or area of resin porosity, a delamination, foreign matter, or a change in stiffness caused by a composite ply formed of a different material, etc. When the high frequency sound wave contacts the discontinuity, a portion of the sound energy is reflected back through the part 102 toward the ultrasonic transducer 106. In one embodiment, the part 102 has a thickness dimension T of approximately ¾ inches, although it is appreciated that the thickness dimensions T may vary on other embodiments to include greater and lesser values.

The ultrasonic probe 106 is gated to act as both a transmitter that produces RF sound wave pulses and as a receiver that records the reflected RF sound wave signals. The time between when an RF pulse is transmitted and an RF reflection is received equals the time it took for the sound wave to pass into the test part 102, contact the area of discontinuity, and travel back to the ultrasonic probe 106. Thus, the time between transmission and reception is related to the depth of the discontinuity in the part 102. The amplitude of the RF signal is related to the magnitude of the discontinuity, as the larger the discontinuity, the more sound energy is reflected back towards the ultrasonic probe 106.

In an automated embodiment, the ultrasonic probe 106 may be located on a mechanical arm whose movement is precisely controlled by the computer 108. In accordance with known test systems, the mechanical arm may move the ultrasonic probe 106 over an outer surface 126 of the test part 102 in a precisely controlled scan during testing. As the ultrasonic probe 106 moves across the test part 102, ultrasonic test data is taken at preprogrammed data points on the part 102, typically at equally spaced apart distances along the length of the part 102, although the computer 108 could alternatively be programmed to take data at irregular distances or intervals to inspect the part 102.

As the ultrasonic probe 106 receives the reflected sound waves at individual data points, the information is passed to the ultrasonic test apparatus 104 in the form of a radiofrequency (RF) signal. This RF signal may be digitized by the ultrasonic test apparatus 104 or the computer 108 using known techniques and the resulting digitized data may be passed to and stored as a data array in a memory associated with the CPU 110. The location on the test part 102 from which each set of digitized data originated can be determined by knowing the scan pattern and by knowing the position of the digitized data in the data array. Data may be displayed to a technician, via the display 112, in a variety of different formats, including but not limited to a pulse echo, an A-Scan, a B-Scan, or a time of flight display familiar to those in the art. During scanning or after testing, the data may be output as a hard copy to be saved for later reference.

Figure 2:
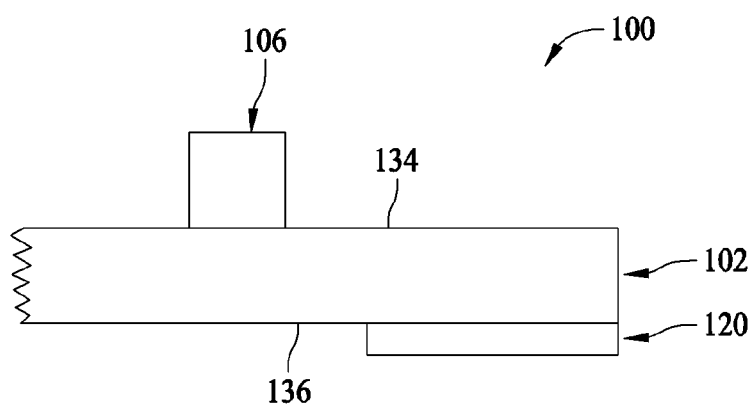
FIG. 2 illustrates a portion of the system shown in FIG. 1 with the test probe in a first location.

FIG. 2 illustrates a portion of the system 100 shown in FIG. 1 with the test probe 106 in a first location relative to the part 102 and a supporting portion of the part holder 120. As shown in FIG. 2, an end portion of the part directly abuts the surface of the part holder 120 and the part 102 lies on the part holder 120 with surface-to-surface engagement. When the probe 106 is positioned relative to the part 102 as shown in FIG. 2 to perform a scan, the scan is taken in a region of the part 102 overhanging the part holder 120. As a result, there is no portion of the part holder 120 underneath the part 102.

Figure 3:
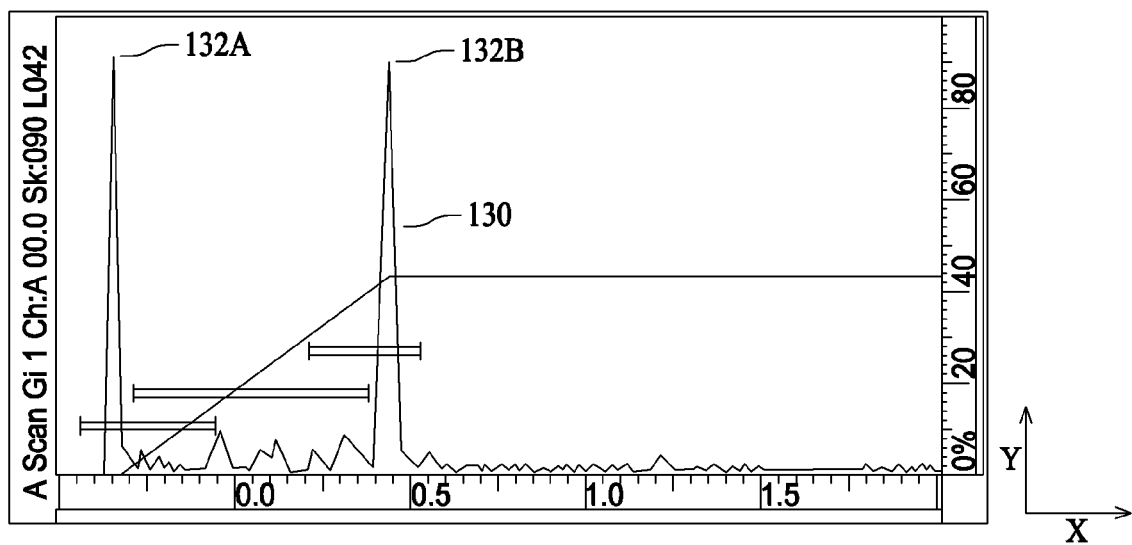
FIG. 3 illustrates an exemplary waveform for the test signal with the probe shown in the position of FIG. 2.

FIG. 3 illustrates an exemplary return signal waveform collected by the ultrasonic probe 106 when the probe 106 is in the position shown in FIG. 2 and displayed to a technician. The digitized RF signal may be displayed as an "A-Scan," a representative example of which is illustrated in FIG. 3. As those in the art will appreciate, an A-Scan is a graph of the reflected RF sound energy signal 130 received by the ultrasonic probe 106 where time is plotted along the horizontal X-axis and amplitude is plotted along the vertical Y-axis. In the actual embodiment of the test system 100 described above, the RF signal 130 was digitized by assigning values from 0 to 100 to the amplitude of the RF signal, the value of 50 being assigned to zero volts.

As discussed above, the greater the discontinuity in the test part 102 the greater the amplitude of sound energy reflected, thus the greater the amplitude of the RF signal 130. In the exemplary A-Scan shown in FIG. 3, the signal 130 includes two portions designated 132A and 132B having the greatest amplitude reflection, sometimes referred to as peaks, that are caused by waves reflected off the upper or front surface 134 (FIG. 2) and the lower or rear surface 136 (FIG. 2), respectively, of the test part 102. The amplitude at each portion 132A and 132B is substantially the same via a known Time Corrected Gain (TCG) function applied by the computer 108. Other reflections in the signal 130 between the signal portions 132A and 132B represent discontinuities through the thickness of the test part 102. These other reflections in the signal 130 may be caused by voids, delaminations, other discontinuities or inconsistencies within the test part, or may alternatively be representative of the individual composite layers forming the test part 102. A trained technician may readily distinguish problematic reflections from non-problematic reflections in the signal 130 between the maximum amplitude portions 132A and 132B. The determination of problematic reflections is, of course, dependant on the construction of the part 102 and its particular specifications.

It is possible to determine the distance between individual reflections between the maximum amplitude portions 132A and 132B and thus the location of discontinuities within the thickness of the test part 102 using the signal 130. Specifically, a time span between any two reflections in the signal 130 of the A-Scan is determined using the horizontal X-axis of the digitized waveform. Knowledge of the time span between the reflections and the speed of sound being propagated through the test part 102 allows the distance between reflections to be calculated.

For example, the time between when an RF pulse is applied to the part 102 as determined by the front surface reflection 132A and when a discontinuity reflection between the front surface reflection 132A and the rear surface reflection 132B is received may be determined with the horizontal X-axis. By multiplying the time difference by the speed of sound propagating in the test part, the total distance that the reflected wave traveled in the part results. Considering that the wave actually propagates to and is reflected from the discontinuity, half of the total distance that the reflected wave traveled in the part represents the distance of the discontinuity from the front surface 134 of the part 102. Thus, a precise location of one or more discontinuities may be determined using an A-Scan waveform at any specific location in the beam, such as the location shown in FIG. 2.

It is recognized, however, that is may be difficult for an operator to fully understand the internal structure of a test part 102 solely from an A-Scan display. The computer 108 is therefore capable of displaying ultrasonic test data in a number of different display formats, and the operator may alter the display formats as desired. Alternative display formats may include a "B-Scan" familiar to those in the art, "a time of flight display" familiar to those in the art, or any other desirable format for detecting discontinuities and analyzing the structure of the test part 102 in detail.

Figure 4:
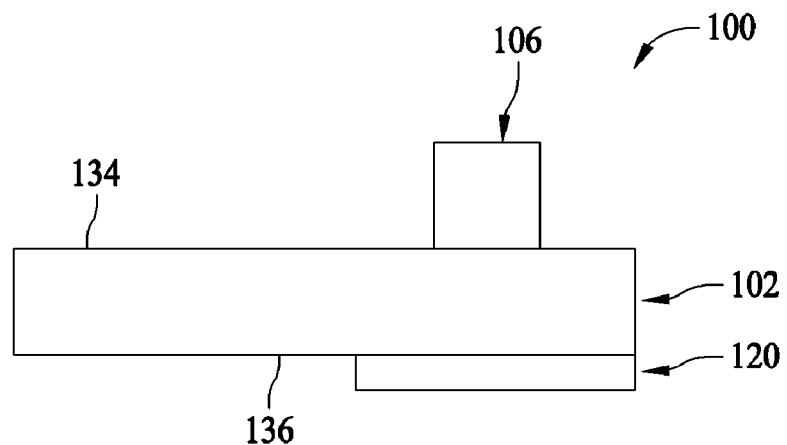
FIG. 4 is similar to FIG. 2 but illustrates the test probe in a second location.

FIG. 4 is a view similar to FIG. 2 but illustrates the test probe 106 in a second location wherein the part 102 at the location of the probe 106 rests directly on the part holder 120. It is in this position that signal interfere may undesirably result.

Figure 5:
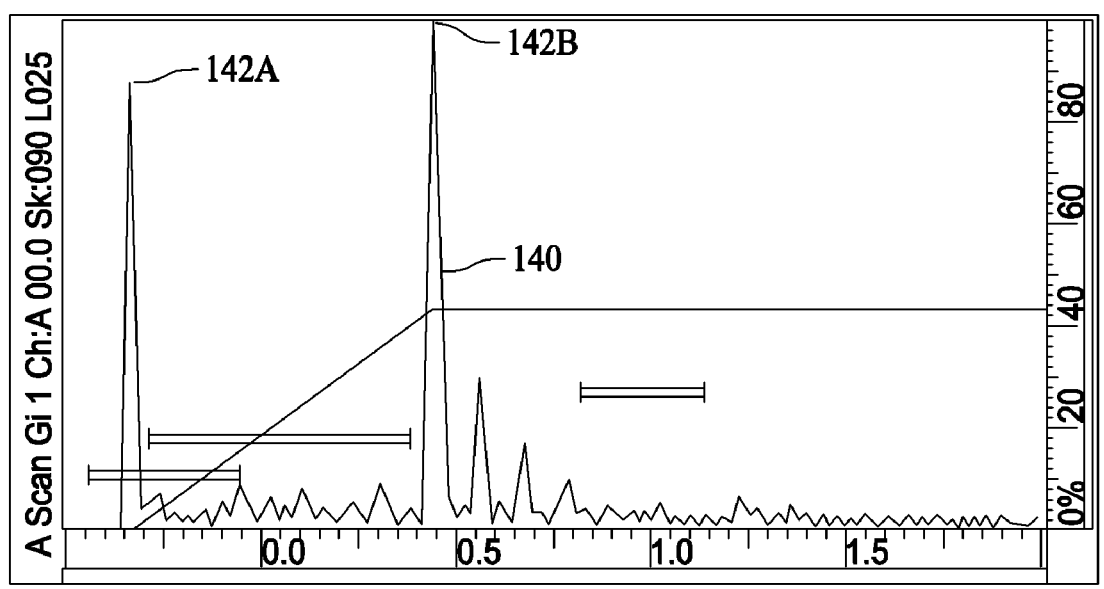
FIG. 5 illustrates an exemplary waveform for the test signal with the probe shown in the position of FIG. 4.

FIG. 5 illustrates an exemplary A-scan waveform for the test signal 140 with the probe 106 in the position shown in FIG. 4. Similar to the signal 130 shown in FIG. 3, the signal 140 includes a first large amplitude reflection 142A caused by the front surface 134 of the part 102.

Unlike the signal 130, the signal 140 includes a second large amplitude reflection 142B that is larger than the first 142A, despite the use of a Time Corrected Gain (TCG) function that in theory would produce equal amplitudes in the portions 142A and 142B. The reflection 142 is larger in FIG. 5 because the part 102 rests directly on surface of the part holder 120. Consequently, a reflection from the back surface 136 of the part 102 is overlaid with a reflection of the surface of the part holder 120 that the part 102 rests against, causing a summation of the amplitude of the two reflected signals. The summation of amplitude attributable to the part holder 120 and amplitude attributable to the part 102 itself distorts the signal 140 from the user's perspective, and is sometimes referred to as interference in the test signal of interest by the presence of the part holder 120. Additionally, and as also shown in FIG. 5, there multiple echoes of the part holder 120 follow the large amplitude portion 142B.

The summation of the reflections in the signal portion 142B distorts the A-scan view, and can perhaps be confusing to operators who fail to appreciate the subtleties of this particular situation wherein the signal portion 142B is effectively combined reflections from the back surface of the part and front surface of the part holder in one signal. The signal 140 in FIG. 5 appears notably different from the signal 130 in FIG. 3, and an operator may mistakenly conclude that the signal 140 is indicative a problem with the part 102 and/or the test system 100 due to unexpected attributes of the signal 140. This is particularly problematic to the extent the operator makes false positive conclusions regarding discontinuities in the part 102 or operation of the system 100, leading to rejected parts 102 or delays in inspecting parts when the parts 102 are otherwise acceptable.

Additionally, and in the example shown in FIG. 5, the signal portion 142 signal is off the scale of the Y-axis. This is undesirable when a loss of back wall gating scheme is being used in signal processing, and may lead to further errors and difficulties in evaluating the test results.

Figure 6:
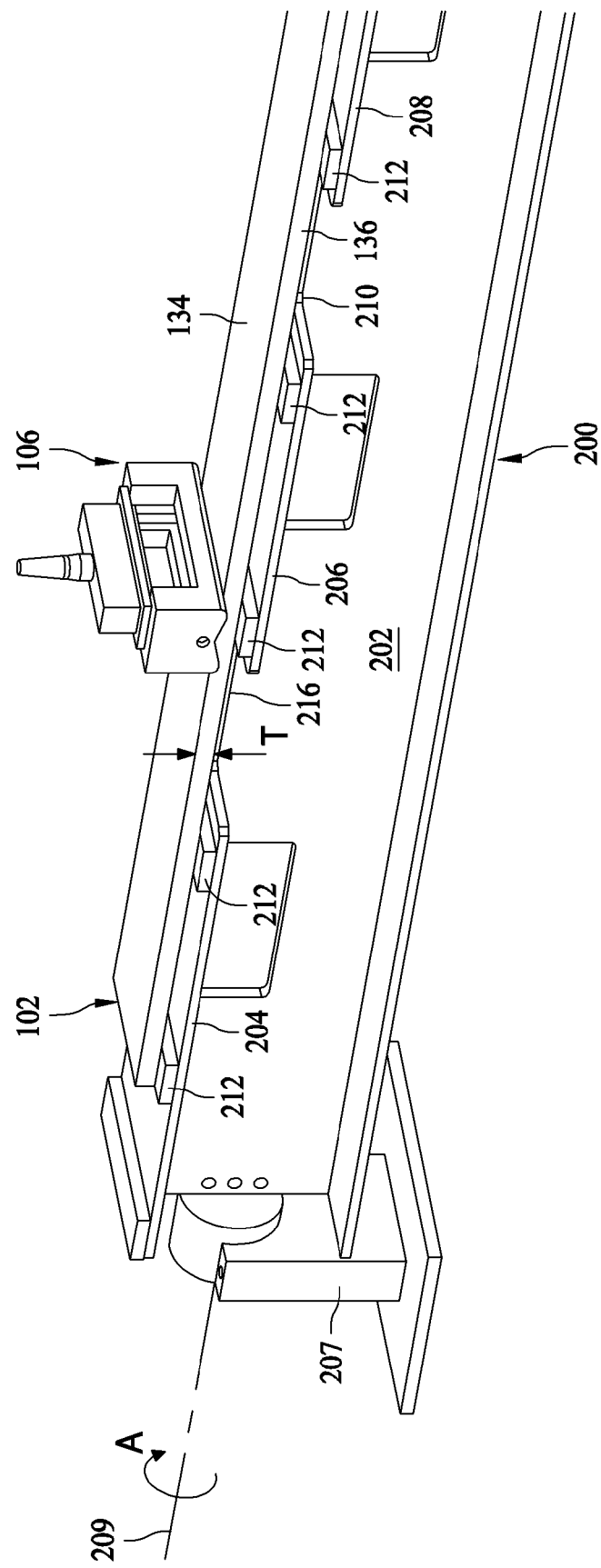
FIG. 6 is a partial perspective view an exemplary part holder for the system shown in FIG. 1.

FIG. 6 is a partial perspective view an exemplary part holder 200 for the system 100 shown in FIG. 1 that avoids the issues described above with respect to signal interference and distortion regardless of the location of the probe 106 relative to the part holder 200. The part holder 200 may be used in the immersion tank 122 instead of the part holder 120 to provide a more reliable test system 100 that is less susceptible to signal interference and distortion, as well as associated errors and delays in the part inspection process.

As shown in FIG. 6, the part holder 200 includes an elongated body 202 including a number of support surfaces 204 for the part 102, or for multiple parts 102, along the axial length of each part 102. For example, one or more long parts 102 may extend on and be supported by all of the support surfaces 204, 206 and 208 wherein the surfaces 204 and 208 support the part 102 on its ends and the support surface 206 supports the part 102 in an intermediate or middle portion between its ends. As another example, several shorter parts may be placed end-to-end on the part holder 200, with the ends of the each part supported on the nearest support surface 204, 206 or 208. Combinations of parts may also be placed side-by-side on the support surfaces 204, 206 and 208.

The body 202 may be rotatably mounted to a base 207 so that the body 202 may be rotated about its longitudinal axis 209 in the direction of arrow A if desired. Rotation of the body 202 in the direction of arrow A facilitates inspection of parts of varying shapes and profiles, as well as provides alternative positioning of the part 102 relative to the probe 106 to inspect different axes of the part 102. In the position shown, the body 202 is rotated to a horizontal position wherein the probe 106 is generally parallel with the upper surface 134 of the part 102. As such, the probe is used to inspect the beam in a direction generally perpendicular to the front surface 106 and in a plane parallel to the dimension T. By rotating the body 202, however, the part 102 may be positioned such that the probe 106 may be used to inspect the part in another plane that is not parallel to the dimension T as desired. Also, a curved part be inspected by rotating the body 202 to one or more different positions for inspection.

As illustrated in FIG. 6, the support surfaces 204 are generally flat and planar, and are parallel to one another to easily support most part geometries. While three support surfaces 204, 206 and 208 are shown in FIG. 6, the body 202 may include additional support surfaces along its length. Cut-out regions 210 are formed into the body in the plane of the support surfaces 204, 206 and 208 that separate the support surfaces 204, 206 and 208 into discrete areas for supporting the part 102 long its length. As such, the part 102 is partly supported over the support surfaces 204, 206 and 208, and in part overhangs or is cantilevered across the cutout regions 210.

To address signal interference and distortion issues, a solid buffer material 212 is placed on the respective support surfaces 204, 206 and 208 and provides an intervening and intermediate buffer layer between the rear surface 136 of the part 102 and the support surfaces 204, 206 and 208 of the part holder 200. The material 212 has acoustic properties approximately equal to the acoustic properties of the immersion fluid 124 used in the immersion tank 122 shown in FIG. 1. As one example, when the immersion fluid 124 is water, the material may be selected to have water-like qualities. Specifically, the buffer material is selected to have an acoustic impedance, or the product of the density of a material and the velocity at which ultrasound passes through it, that closely matches the acoustic impedance of the immersion fluid, water being one example. When the acoustic impedance of the immersion fluid 124 and the buffer material 212 are approximately equal, the buffer material is rendered acoustically invisible to ultrasonic testing in a pulse echo mode. The acoustic invisibility of the buffer material 212 effectively separates the signal reflections from the rear surface 136 of the part 102 and the signal reflections for the support surfaces 206, 208 and 210 of the part holder 200.

One such suitable buffer material 212 is an AQUALENE™ elastomer material that was developed for ultrasonic testing purposes for dry-coupled testing, as opposed to the wet-coupled testing in an immersion tank as presently described. AQUALENE™ material is a rubber-like material available from Materials Research Institute of Ontario, Canada. The AQUALENE™ material is described in the published Application for Canadian Patent No. 2,127,039, which explains that the material includes an elastomer originally developed for use as a dry ultrasonic couplant, and has ultrasonic properties very near those of water. The AQUALENE™ material is a blend of isomers of a branched homopolymer in which the amount of cross-linking is controlled at high temperature and pressure. As a result of the controlled cross-linking the range of temperatures over which the polymer exists in the so-called rubbery state is extended. Proper selection of cross-link initiator permits the entrapment of a long chain alcohol, which tends to enhance acoustic transmittance. The elastomer in the AQUALENE™ material is flexible to accommodate rough surfaces and various geometries, and is generally clear and colorless. It is provided in solid form, and was originally developed to provide an effective coupling medium for ultrasonic testing while avoiding the inconvenience, and perceived drawbacks, of coupling fluids such as water. AQUALENE™ couplant products are available in many sizes and thicknesses, and custom designs are also available.

While AQUALENE™ material is specifically noted for use as the buffer material 212 on the part holder 200, other materials are known having hydrophilic polymers that closely parallel the acoustic properties of water, for example, that may alternatively be used. In other embodiments using other coupling fluids for wet-coupled ultrasonic testing, still other materials having similar acoustic properties matching the coupling fluid may be utilized.

In the illustrated embodiment, the buffer material 212 is applied to only a portion of the respective support surfaces 204, 206 and 208. Specifically, and as shown in FIG. 6, the buffer material 212 is applied to the surfaces in relatively small rectangular strips having, for example, about ¼ inch thickness, that are bonded to the support surfaces 204, 206 and 208 using an epoxy, adhesive or other bonding agent. The strips extend transversely to the axial length of the part 102. Each support surface 204, 206 and 208 of the part holder 200 may include two strips of buffer material 212 positioned roughly near the ends of each support surface 204, 206 and 208, with the remainder of each support surface 204, 206 and 208 generally free of the buffer material 212. In the exemplary embodiment, no buffer material 212 is used on the front surface 134 of the part 102 along which the probe 106 is moved to inspect the part 102.

While one exemplary embodiment has been described that utilizes two small strips of buffer material 212 on each support surface 204, 206 and 208, it is recognized that that buffer material 212 may alternatively be provided in another manner, including but not limited to greater or fewer numbers of strips of material 212 that may cover greater or lesser portions of the support surfaces 204, 206 and 208 of the part holder 200. Additionally, the material 212 need not be applied in the form of "strips" at all, and may be shaped in other geometric configurations, such as circles positioned at desired locations of testing with the radius of the circle spanning the width of the part. Likewise, polygonal shapes of material 212 may be used if desired to obtain further variation. While lesser amounts of buffer material 212 may be preferred for cost reasons, the functional benefit of the material 212 with respect to signal quality issues, described below, is not dependent on the amount of material 212 used.

Figure 7:
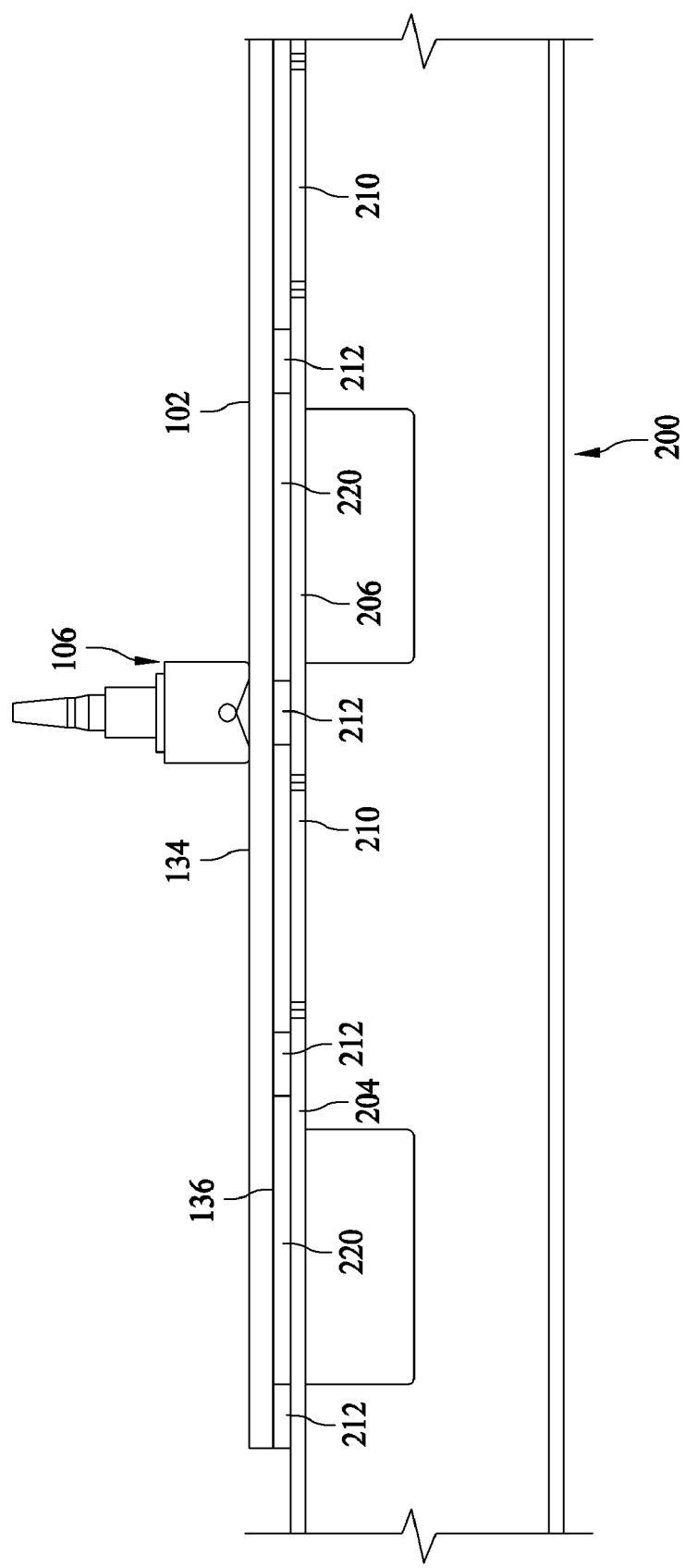
FIG. 7 is a partial side elevational view of the part holder shown in FIG. 6.

As best seen in FIG. 7, the strips of buffer material 212 which extend only on a portion of the support surfaces 204, 206 and 208 of the part holder 200, serve as standoffs that physically separate the rear surface 136 of the part 102 from the support surfaces 204, 206 and 208 of the part holder. Between the strips of buffer material are gaps 220 where the rear surface 136 of the part 102 remains separated from the support surfaces 204, 206 and 208, yet is not directly supported by the buffer material 212. That is the part 102 overhangs the buffer material 212 in the vicinity of the gaps 220, while the part 102 rests against the buffer material 212 where the strips are applied and the buffer material 212 is directly supported on the strips. In an exemplary embodiment, the rear surface 136 of the part 102 is frictionally engaged to the buffer material 212 without any external structure to retain or the secure the part 102 in place, although external securing structure may be used in other embodiments provided that such securing structure does not itself present signal interference issues.

In use, when the part holder 200 and part 102 are submerged in the fluid 124 in the tank 122 (FIG. 1), the gaps 220 between the strips of buffer material 212 are filled with the immersion fluid. Because the acoustic properties of the fluid 124 and the buffer material 212 approximately match one another, an acoustic path beneath the rear surface 136 of the part 102 is substantially the same over the entire area of the support surfaces 204, 206 and 208 of the part holder 200. The entire length of the part 102 over the support surfaces 204, 206 and 208 appears to be floating on a layer of immersion fluid in ultrasonic scans taken at locations over the support surfaces 204, 206 and 208.

Figure 8:
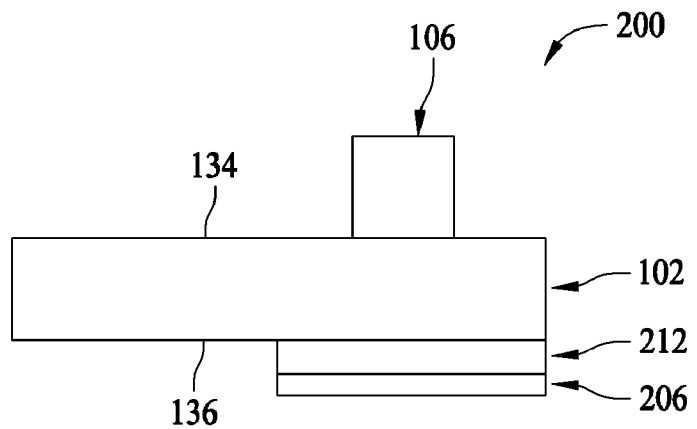
FIG. 8 illustrates a portion of the part holder shown in FIGS. 6 and 7 with the test probe in the second location.

FIG. 8 illustrates a portion of the part holder 200 with the test probe in the second location similar to that shown in FIG. 4. That, is the probe is located directly over one of the support surfaces, such as the support surface 206, of the part holder 200. The buffer material 212, unlike the situation represented in FIG. 4, intervenes and separates the part 102 from the support surface 206. The buffer material 212 is sandwiched between the part 102 and the support surface 206 and is in intimate, direct, surface-to-surface engagement with each. Ultrasonic waves generated by the probe 106 are passed first through the part 102 and secondly through the solid buffer material 212 to separate echoes from the part 102 from echoes of the support surface 206. The passage of the waves through the solid buffer material 212 creates an acoustic delay between a return echo of the part 102 and a return echo of the part holder 200 as explained below.

Figure 9:
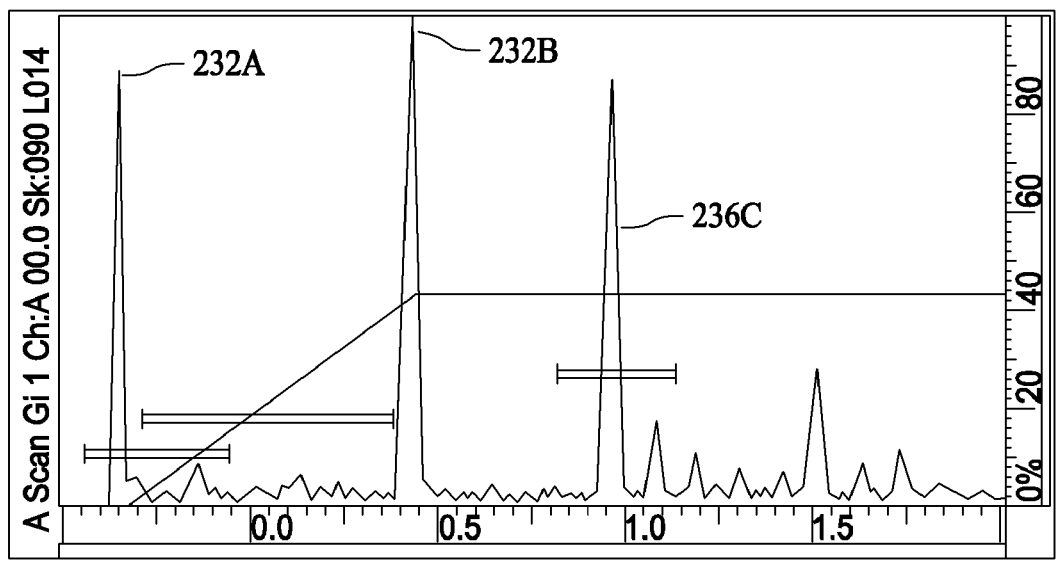
FIG. 9 illustrates an exemplary waveform for the test signal with the probe shown in the position of FIG. 8.

FIG. 9 illustrates an exemplary A-Scan waveform for the test signal with the probe 106 shown in the position of FIG. 8. As shown in FIG. 9, the signal 230 includes a first large amplitude portion 232A that is caused by waves reflected off the upper or front surface 134 (FIG. 8) of the part 102, and a second large amplitude portion 232B that is caused by waves reflected off the lower or rear surface 136 (FIG. 8) of the part 102. Reflections in the signal 230 between the signal portions 232A and 232B represent discontinuities through the thickness of the test part 102.

The back surface signal amplitude in the portion 232B has increased relative to the front surface signal amplitude in the portion 232A by approximately 10% of screen height, which is significantly less than the off-scale increase of the portion 142B shown in FIG. 5 for the same part 102 wherein the buffer material 212 was not present between the part 102 and the support surface of the part holder.

The third signal spike 236C in FIG. 9 is caused by reelections from the support surface 206 of the part holder 200. The portion 236C is now separated from portion 232B from the back surface 136 of the part 102 by virtue of the buffer material 212, unlike the waveform of FIG. 5 wherein reflections from the part back surface and the part holder support surface are combined into a single signal. The multiple echoes from the part holder that occur subsequent to the portion 236C (to the right in FIG. 9) are now unlikely to interfere with any gating schemes used to perform ultrasonic tests. Since in practice, multiple parts 102 can be examined at once on the same part holder 200, there are now multiple echoes from the part holder that can be eliminated with the buffer material 212.

Improved signal quality afforded by the buffer material 212 allows increases in the sensitivity of the scanning system by allowing gating schemes to be used that previously could not be used due to interference issues. Increased sensitivity of the scanning system, in turn, facilitates an enhanced ability to find, detect, and locate discontinuities in inspected parts 102. Waste and inefficiencies attributable to false positive indications of discontinuities is also minimized, if not entirely avoided. Further benefits include reduced costs for tooling to inspect parts as the part holder 200 is more universally applicable to a large variety of parts, and increase production rates of inspection processes.

While the part holders, systems and methods of separating signals have been described in terms of various specific embodiments, those skilled in the art will recognize that the concepts presented herein can be practiced with modification within the spirit and scope of the claims.

What is claimed is:

1. A part holder for ultrasonic testing of a part to be inspected that is immersed in a fluid, the part being inspected with an ultrasonic scanning probe, the part holder comprising:

at least a first surface for holding of the part in a predetermined orientation relative to the ultrasonic scanning probe; and a portion of the first surface provided with a solid buffer material having acoustic properties approximately equal to the immersion fluid, the solid material separating a surface of the part from the first surface to reduce signal distortion caused by the first surface.

2. The part holder of claim 1, wherein the solid buffer material comprises one of an elastomeric material and a hydrophilic polymer.

3. The part holder of claim 1, wherein the solid buffer material comprises a first strip and a second strip spaced from one another on the first surface.

4. The part holder of claim 1, wherein the first surface is substantially planar.

5. The part holder of claim 1, wherein the part holder is rotatable about a longitudinal axis thereof to adjust the predetermined position.

6. The part holder of claim 1, wherein the part holder further comprises at least a second surface for holding of the part in a predetermined orientation relative to the ultrasonic scanning probe, the second surface separated from the first surface and spaced from the first surface, and the second surface provided with the solid buffer material to separate a surface of the part from the second surface.

7. The part holder of claim 6, wherein the part holder comprises at least a third surface for holding of the part in a predetermined orientation relative to the ultrasonic scanning probe, the third surface separated from the first and second surfaces and spaced from each of the first and second surfaces, and the third surface also provided with the solid buffer material to separate a surface of the part from the third surface.

8. The part holder of claim 7, wherein the second surface is positioned between the first and third surfaces, the first and third surfaces supporting an end portion of the part and the second surface supporting a portion of the part between the end portions.

9. The part holder of claim 1, wherein the part is retained to the solid buffer material solely by frictional forces.

10. The part holder of claim 1, wherein the solid buffer material exhibits the acoustic properties of water.

11. An ultrasonic test system for the inspection of a variety of differently shaped parts, the test system comprising:

an immersion tank constructed to be filled with an immersion fluid;

a part holder in the immersion tank, the part holder comprising a plurality of surfaces for maintaining the part in a predetermined position within the tank, each of the surfaces being provided with a solid buffer material covering at least a portion of the respective surface thereof, the solid buffer material defining raised support surfaces for the part and the solid buffer material having acoustic properties approximately equal to acoustic properties of the immersion fluid; and an ultrasonic probe movable along an outer surface of the part when the part is placed upon the raised support surfaces;

wherein ultrasonic waves generated by the probe are passed first through the part and secondly through the solid buffer material to separate echoes from the part from echoes of the surfaces of the part holder.

12. The test system of claim 11, wherein the solid buffer material comprises one of an elastomeric material and a hydrophilic polymer.

13. The test system of claim 11, wherein each of the surfaces of the part holder are substantially flat.

14. The test system of claim 11, wherein the surfaces of the part holder are separated from one another along a length of the part.

15. The test system of claim 11, wherein the solid buffer material is applied to the surfaces of the part holder in strips separated from one another.

16. The test system of claim 11, wherein the surfaces of the part holder support the part on a first end, a second end, and an intermediate portion between the first end and the second end.

17. The test system of claim 11 wherein the part holder is rotatable to selectively position the surfaces at different angles relative to the ultrasonic probe.

18. A method of inspecting parts with an ultrasonic test system, the ultrasonic test system including an ultrasonic probe, an immersion tank and an immersion fluid in the tank, a part holder submerged in the immersion tank, the part holder having a plurality of separated surfaces thereon for accommodating a variety of parts to be inspected, the part holder being rotatable to selectively position the surfaces of the part holder relative to the ultrasonic probe, the method comprising:

positioning a part upon at least two surfaces of the part holder;

rotating the part to a desired position relative to the ultrasonic probe;

utilizing the ultrasonic probe to generate a high frequency sound wave near a surface of the part;

collecting return echoes of the part with the ultrasonic probe; and separating the return echoes of the part from the return echoes of the at least two surfaces of the part holder by creating an acoustic delay between a return echo of the part and a return echo of the part holder.

19. The method of claim 18, wherein separating of the return echoes by creating an acoustic delay comprises:

providing the at least two surfaces with a solid material having acoustic properties approximately equal to the acoustic properties of the immersion fluid, the solid material extending between the surfaces of the part holder and the part.

20. The method of claim 19, wherein providing the at least two surfaces with a solid material comprises applying strips of the solid material to the surfaces of the part holder.

* * * * *